(12) United States Patent
Alisi et al.

(10) Patent No.: US 8,519,139 B2
(45) Date of Patent: Aug. 27, 2013

(54) INDAZOLAMIDES WITH ANALGESIC ACTIVITY

(75) Inventors: Maria Alessandra Alisi, Rome (IT); Nicola Cazzolla, Albano Laziale (IT); Angelo Guglielmotti, Rome (IT); Guido Furlotti, Rome (IT); Giuseppe Luna, Cecchina (IT); Lorenzo Polenzani, Grottaferrata (IT)

(73) Assignee: Aziende Chimeche Riunite Angelini Francesco A.C.R.A.F. S.p.A., Rome (IT)

( * ) Notice: Subject to any disclaimer, the term of this patent is extended or adjusted under 35 U.S.C. 154(b) by 683 days.

(21) Appl. No.: 12/607,463

(22) Filed: Oct. 28, 2009

(65) Prior Publication Data
US 2010/0048907 A1    Feb. 25, 2010

Related U.S. Application Data

(62) Division of application No. 10/541,209, filed as application No. PCT/EP2004/000647 on Jan. 26, 2004, now Pat. No. 7,632,849.

(30) Foreign Application Priority Data

Feb. 18, 2003   (IT) .............................. MI2003A0287

(51) Int. Cl.
  *C07D 211/26*   (2006.01)
(52) U.S. Cl.
  USPC ........................................................ 546/229
(58) Field of Classification Search
  USPC ........................................................ 546/229
  See application file for complete search history.

(56) References Cited

U.S. PATENT DOCUMENTS

| 3,705,175 | A | 12/1972 | Magdanyi et al. | 544/371 |
| 5,654,320 | A | 8/1997 | Catlow et al. | 514/322 |
| 6,096,476 | A | 8/2000 | Yanagida et al. | 430/270.1 |
| 6,096,746 | A | 8/2000 | Suzuki et al. | 514/254.06 |
| 6,770,650 | B2 | 8/2004 | Gong et al. | 514/253.01 |

FOREIGN PATENT DOCUMENTS

| EP | 0 732 333 | 9/1996 |
| EP | 0 908 459 | 4/1999 |
| EP | 0 975 623 | 2/2000 |
| WO | 98/07728 | 2/1998 |

OTHER PUBLICATIONS

CHEMCATS An:0073079075 (2011).*
Alisi et al. "Indazol . . . " CA141:243550 (2004).*
CHEMCATS 0071688244; 0071672197; 0071577983 (2011).*
Alisi et al. "Indazolamides . . . " CA 141:243550 (2004).*
Alisi et al. "Indazolamines . . . " CA141:243550 (2004).*
DeRamaix "Relative pK . . . " CA49:11919 (1955).*
Hach "Local anestetics . . . " CA49:4725 (1955).*
Jacob et al. "The quaternary . . . " CA9:13140 (1915).*
Kempter et al. "Synthesis of . . . " CA100:139066 (1984).*
Englen, et al., "Central 5HT4 receptors" Trends in pharmacol. sci. v. 16(1111) p. 391-398 (1995).
Schaus, et al., "Synthesis and structure-activity relationships . . . " J. Med. Chem.. v.41, p. 1943-1955 (1998).
Ashburn, Michael A.: "Management of chronic pain", The Lancet, vol. 353, pp. 1865-1869, May 29, 1999.
Wall, Patrick D.; Melzack, Ronald Eds.: Textbook of Pain, Fourth Edition, Churchill Livingstone, 1999.
Scholz, Joachim; Woolf, Clifford J.: "Can we conquer pain?", Nature Neuroscience Supplement, vol. 5, pp. 1062-1067, Nov. 2002.
Prugh, John D.: "A Simple Method of Protecting a Secondary Amine with tert Butyloxycarbonyl (BOC) in the Presence of a Primary Amine", Synthetic Communications, vol. 22, No. 16, pp. 2357-2360, 1992.
Corsi, Giorgio: "1-Halobenzyl-1H-indazole-3-carboxylic acids. A New Class of Antispermatogenic Agents", Journal of Medicinal Chemistry, vol. 19, No. 6, pp. 778-783, 1976.
Larock, Richard C.: "Comprehensive Organic Transformations", VCH, pp. 965-966, (1989).
J.O.C., vol. 23, p. 621, Apr. 1958.
Trivedi, J.P.: "Potential Local Anaesthetics: Synthesis of Benzyloxy-Acetanilides and Propionanilides", Indian J. Appl. Chem., vol. 30, Nos. 3-4, pp. 91-95, 1967.
Buu-Hoi, N. P.: "Indazole-3-carboxylic Acids and their Derivatives", Institut de Chimie des Substances Naturelles du C.N.R.S., J. Heterocyclic Chem., vol. 1, No. 5, pp. 239-241, Dec. 1964.
Randall, Lowell O.: "A Method for Measurement of Analgesic Activity on Inflamed Tissue", Arch. Int. Pharmacodyn. Ther., vol. 111, pp. 409-419, 1957.
Andrew, David: "Mechanical and Heat Sensitization of Cutaneous Nociceptors After Peripheral Inflammation in the Rat", J. Neurophysiol., vol. 82, No. 5, pp. 2649-2656, 1999.
Takatani, et al., "Fused inmidazopyridine . . . " CA 128:3692 (1997).
Hargreaves, K.: "A new and sensitive method for measuring thermal nociception in cutaneous hyperalgesia", Pain, vol. 32, pp. 77-88, 1988.
Courteix, C.: Streptozocin-induced diabetic rats: behavioural evidence for a model of chronic pain, Pain, vol. 53, pp. 81-88, 1993.
Bannon, A. W.: "ABT-594, a novel cholinergic channel modulator, is efficacious in nerve ligation and diabetic neuropathy models of neuropathic pain", Brain Research, vol. 801, pp. 158-163, 1998.
U.S. Appl. No. 12/638,470, filed Dec. 15, 2009, Alisi, et al.

* cited by examiner

*Primary Examiner* — Celia Chang
(74) *Attorney, Agent, or Firm* — Oblon, Spivak, McClelland, Maier & Neustadt, L.L.P.

(57) ABSTRACT

The present invention relates to compounds of formula (II)

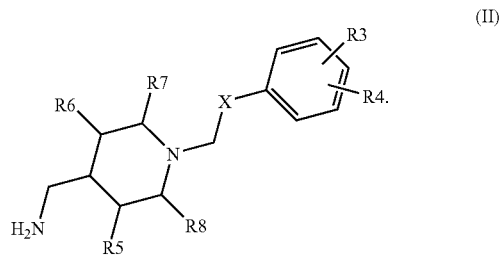

(II)

16 Claims, No Drawings

INDAZOLAMIDES WITH ANALGESIC ACTIVITY

CROSS-REFERENCE TO RELATED APPLICATIONS

The present application is a divisional of U.S. application Ser. No. 10/541,209, filed on Jul. 5, 2005, which is a National Stage (371) of PCT/EP04/00647, filed on Jan. 26, 2004, and claims priority to Italian application MI2003A000287, filed on Feb. 18, 2003, the entire contents of these applications are incorporated herein by reference.

The present invention relates to indazolamides endowed with analgesic activity, to a method for the preparation thereof and to a pharmaceutical composition containing the same.

Chronic pain is very widespread. On average, about 20% of the adult population suffers from this. This type of pain is generally associated with chronic lesions and/or degenerative processes. Typical examples of pathologies characterized by chronic pain are rheumatoid arthritis, osteoarthritis, fibromyalgia, neuropathies, etc. [Ashburn M A, Staats P S, Management of chronic pain. Lancet 1999; 353: 1865-69].

The analgesic drugs currently used belong essentially to two classes: non-steroidal anti-inflammatories (NSAIDs), which combine the analgesic activity with anti-inflammatory activity, and opioid analgesics. These classes constitute the bases for the "analgesic scale" with three grades, proposed by the World Health Organisation for the pharmacological treatment of pain [Textbook of pain. Fourth edition. P. D. Wall and R. Meizack Eds. Churchill Livingstone, 1999].

Chronic pain is often debilitating and causes loss of ability to work and poor quality of life. It therefore has consequences in terms of both economic and social impacts. In addition, there is a significant number of patients whose pain condition still does not have a suitable treatment [Scholz J, Woolf C J. Can we conquer pain? Nat Neurosci. 2002 November; 5 Suppl: 1062-7].

The extensive research efforts devoted towards identifying a suitable analgesic compound have not yet led to appreciable results.

It has now been found, surprisingly, that a novel family of indazolamides has these properties.

In a first aspect, the present invention thus relates to an indazolamide of formula I:

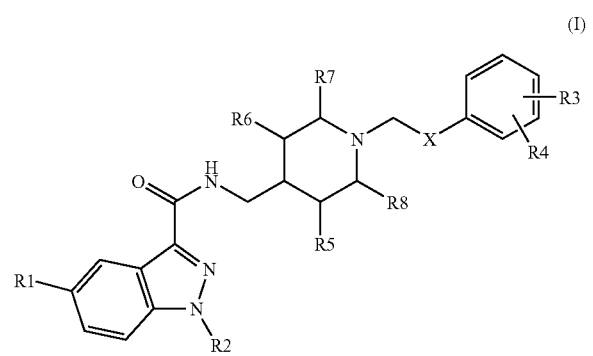

(I)

wherein
X is an NHC(O) or C(O)NH group,
R1 is a hydrogen or halogen atom, or an aminocarbonyl, acetylamino, sulphonylmethyl, aminosulphonylmethyl, linear or branched $C_{1-3}$ alkyl or $C_{1-3}$ alkoxy group,
R2 is a hydrogen atom or a linear or branched $C_{1-6}$ alkyl group or an aryl($C_{1-3}$)alkyl group in which the abovementioned groups are optionally substituted with one or more substituents chosen from the group comprising halogen atoms, $C_{1-3}$ alkyl and $C_{1-3}$ alkoxy,
R3 and R4, which may be identical or different, are a hydrogen or halogen atom, or an amino, nitro, hydroxyl, linear or branched $C_{1-3}$ alkyl, $C_{1-3}$ alkoxy, di($C_{1-3}$)alkylamino, acetylamino or O—($C_{1-3}$)alkylphenyl group, or R3 and R4, together, form a 5- to 7-membered ring in which one or two of the said members may be a hetero atom chosen from N, S and O,
R5, R6, R7 and R8, which may be identical or different, are H or methyl;
and the acid-addition salts thereof with pharmaceutically acceptable organic and mineral acids.

Preferred meanings of R1 are H, methyl and methoxy.
Preferred meanings of R2 are H, methyl and isopropyl.
Preferred meanings of R3 are H, methyl, hydroxyl, amino and dimethylamino.
Preferred meanings of R4 are H, methyl and hydroxyl.
A preferred meaning of R5, R6, R7 and R8 is H.

The analgesic activity of the compounds of formula (I) was demonstrated by means of two experimental models in rats: mechanic hyperalgesia induced by CFA and mechanical hyperalgesia in diabetic neuropathy induced by streptozotocin.

As is known in the prior art, the abovementioned experimental models may be considered as predictive of the activity in man.

CFA-induced hyperalgesia represents a syndrome characterized by the activation of circuits devoted to controlling the inflammatory response and associated with the appearance of conditions that interfere with the perception of pain. Specifically, the injection of CFA is capable of inducing peripherally the release of the "inflammatory soup" (mediators of the inflammatory response and algogenic agents) responsible for the local injury, and centrally, in the spinal cord, biochemical changes that sustain the amplification of the perception of pain. As is well known, this model constitutes a valid tool for studying drugs for use in the treatment of inflammatory pain in man and, in particular, in controlling conditions such as hyperalgesia and allodynia.

Typical examples of human pathologies characterized by this type of pain associated with degenerative inflammatory processes are rheumatoid arthritis and osteoarthritis.

For its part, diabetic neuropathy induced by streptozotocin in rats represents an insulin-dependent syndrome characterized by a concomitant reduction in the speed of conduction of the motor and sensory nerves and the appearance of a series of abnormalities in the perception of pain. As is well known, this experimental model constitutes a useful tool for studying drugs for use in the treatment of neuropathic pain in man. In particular, the model represents a valid example of a large group of types of neuropathic pain characterized by phenomena such as hyperalgesia and allodynia consequent to primary lesions or dysfunctions of the nervous system. Typical examples of human pathologies characterized by dysfunctions of this type and by the presence of neuropathic pain are diabetes, cancer, immunodeficiency, trauma, ischemia, multiple sclerosis, sciatica, neuralgia of the trigeminal nerve and post-herpetic syndromes.

In a second aspect, the present invention relates to a process for preparing the compounds of formula (I) and the acid-addition salts thereof with pharmaceutically acceptable organic and mineral acids, characterized in that it comprises the following stages:

a) condensing an amine of the formula (II)

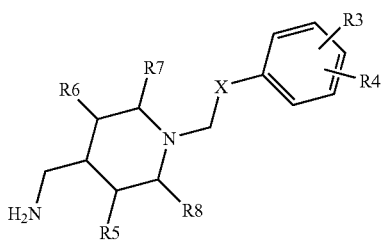

in which
X, R3, R4, R5, R6, R7 and R8 have the meanings given above,
with an indazolecarboxylic acid derivative of formula (IIIa)

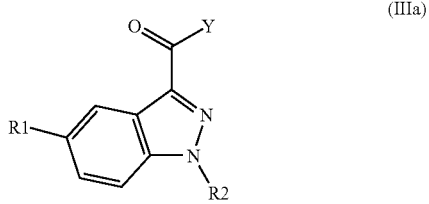

in which
R1 and R2 have the meanings given above, and
Y is a Cl or Br atom, or a group OR or OC(O)R, in which R is an alkyl with a linear or branched chain containing from 1 to 6 carbon atoms,
or of formula (IIIb)

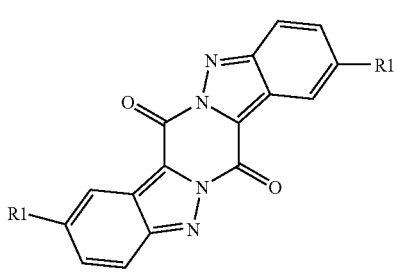

in which
R1 has the meanings given above, to give the indazolamide of formula (I), and
b) optionally, forming an acid-addition salt of the indazolamide of formula (I) with a pharmaceutically acceptable organic or mineral acid.

The amine of formula (II) may be obtained according to conventional methods, for example by alkylation of isonipecotamide with a suitable halide, followed by reduction of the amide to a primary amine (WO 98/07728) or by protecting the aminomethylpiperidine with benzaldehyde (Synthetic Communications 22(16), 2357-2360, 1992), alkylation with a suitable halide and deprotection.

The intermediate of formula (II) in which X, R3, R4, R5, R6, R7 and R8 have the meanings given above is novel.

In a third aspect, the present invention thus relates to an intermediate of formula (II) in which X, R3, R4, R5, R6, R7 and R8 have the meanings given above.

The indazoles of formulae (IIIa) and (IIIb) may also be obtained according to conventional methods. For example, the compounds of formula (IIIa) in which Y is chlorine may be obtained with thionyl chloride from the corresponding acid (J. Med. Chem., 1976, Vol. 19 (6), pp. 778-783), while the compounds of formula (IIIa) in which Y is OR or OC(O)R may be obtained by known esterification reactions or known reactions for forming mixed anhydrides (R. C. Larock, Comprehensive Organic Transformations, VCH, pp. 965-966). In turn, the compounds of formula (IIIb) may be obtained according to J. O. C. 1958, Vol. 23 p. 621.

In one embodiment of the process of the present invention, stage (a) is performed by reacting a compound of formula (II) with a compound of formula (IIIa) in which Y is chlorine with a compound of formula (IIIb) in the presence of a suitable diluent and at a temperature in the range between 0 and 140° C. for a time in the range between 0.5 and 20 hours.

Preferably, the reaction temperature is in the range between 15 and 40° C. Advantageously, the reaction time ranges from 1 to 14 hours.

Preferably, the diluent is aprotic, polar or apolar. Even more preferably, it is an aprotic apolar diluent. Examples of suitable aprotic apolar diluents are aromatic hydrocarbons, for instance toluene. Examples of suitable aprotic polar diluents are dimethylformamide and dichloromethane.

In the embodiment in which a compound of formula (IIIa) is used, in which Y is Cl or Br, the abovementioned stage (a) may be performed in the presence of an organic or mineral acid acceptor.

Examples of suitable organic acid acceptors are pyridine, triethylamine and the like. Examples of suitable mineral acid acceptors are alkali metal carbonates and bicarbonates.

According to the process of the present invention, in stage (b), the addition of a pharmaceutically acceptable organic or mineral acid to an indazolamide of formula (I), obtained in stage a) is preferably preceded by a stage of isolating the said indazolamide.

Typical examples of pharmaceutically acceptable acids are: oxalic acid, maleic acid, methanesulphonic acid, para-toluenesulphonic acid, succinic acid, citric acid, tartaric acid, lactic acid, hydrochloric acid, phosphoric acid, sulphuric acid.

In a fourth aspect, the present invention relates to a pharmaceutical composition containing an effective amount of a compound of formula (I), or an addition salt thereof with a pharmaceutically acceptable acid, and at least one pharmaceutically acceptable inert ingredient.

A typical example of a pathological condition that may be usefully treated with a pharmaceutical composition according to the present invention is chronic pain. Typically, this chronic pain is referable to chronic lesions or to degenerative processes, for example rheumatoid arthritis, osteoarthritis, fibromyalgia, oncology pain, neuropathic pain and the like.

Preferably, the pharmaceutical compositions of the present invention are prepared in the form of suitable dosage forms.

Examples of suitable dosage forms are tablets, capsules, coated tablets, granules, solutions and syrups for oral administration; creams, ointments and medicated patches for topical administration; suppositories for rectal administration and sterile solutions for injectable, aerosol or ophthalmic administration.

Advantageously, these dosage forms will be formulated so as to ensure a controlled release over time of the compound of formula (I) or of a salt thereof with a pharmaceutically acceptable acid. Specifically, depending on the type of treatment, the required release time may be very short, normal or sustained.

The dosage forms may also contain other conventional ingredients, such as: preserving agents, stabilizers, surfactants, buffers, salts for regulating the osmotic pressure, emulsifiers, sweeteners, colorants, flavourings and the like.

In addition, when required for particular treatments, the pharmaceutical composition of the present invention may contain other pharmacologically active ingredients whose simultaneous administration is useful.

The amount of compound of formula (I) or of a salt thereof with a pharmaceutically acceptable acid in the pharmaceutical composition of the present invention may vary within a wide range depending on known factors, for instance the type of disease to be treated, the seriousness of the disease, the patient's body weight, the dosage form, the selected route of administration, the number of daily administrations and the efficacy of the selected compound of formula (I). However, the optimum amount may be readily and routinely determined by a person skilled in the art.

Typically, the amount of compound of formula (I) or of a salt thereof with a pharmaceutically acceptable acid in the pharmaceutical composition of the present invention will be such as to ensure a level of administration of between 0.001 and 100 mg/kg/day. Even more preferably, the amount will be between 0.1 and 10 mg/kg/day.

The dosage forms of the pharmaceutical composition of the present invention may be prepared according to techniques that are well known to pharmaceutical chemists, including mixing, granulation, tabletting, dissolution, sterilization and the like.

The examples that follow serve to illustrate the invention without, however, limiting it.

In the examples that follow, the substituents on the aromatic ring (R3 and R4) are indicated with the numbering in bold.

EXAMPLE 1

2-(4-(aminomethyl)-1-piperidyl)-N-phenylacetamide dihydrochloride (AF3R279)

Compound II: R3=R4=R5=R6=R7=R8=H, X=C(O)NH a) N-hexahydro-4-pyridylmethyl-N-phenylmethylideneamine Benzaldehyde (12.7 g; 0.12 mol) was added dropwise to a solution of 4-aminomethylpiperidine (13.7 g; 0.12 mol) in toluene (50 ml).

The solution thus obtained was stirred at room temperature. After 3 hours, the solvent was removed by evaporation under reduced pressure and the residue was taken up twice with toluene (2×50 ml).

N-Hexahydro-4-pyridylmethyl-N-phenylmethylidineamine (25 g) was thus obtained, and was used without further purification.

b) 2-(4-(aminomethyl)-1-piperidyl)-N-phenylacetamide

The product prepared as described in stage a) above (26.3 g; 0.13 mol) was dissolved in absolute ethanol (100 ml) and added to a suspension containing N-2-chloroacetylaniline (22.4 g; 0.13 mol), prepared as described in Beilstein (I) Syst. No 1607, p. 243, and anhydrous potassium carbonate (33 g; 0.24 mol) in absolute ethanol (250 ml).

The suspension thus obtained was refluxed for 16 hours. The reaction mixture was allowed to cool to room temperature and filtered. The filtrate was evaporated under reduced pressure and the residue thus obtained was suspended in 3N HCl (90 ml) and stirred at room temperature for 2 hours.

The solution was transferred into a separating funnel and the acidic aqueous phase was washed 4 times with ethyl acetate (4×50 ml). The aqueous phase was basified to pH 13 with 6N NaOH and extracted with dichloromethane (80 ml). The organic phase was dried over $Na_2SO_4$ and the solvent was removed by evaporation under reduced pressure to give 2-(4-(aminomethyl)-1-piperidyl)-N-phenylacetamide (10 g).

c) 2-(4-(aminomethyl)-1-piperidyl)-N-phenylacetamide dihydrochloride

The product prepared as described in stage b) above (4 g) was converted into the corresponding dihydrochloride by dissolving in ethanol (60 ml), adding hydrochloric ethanol (5 ml) and crystallizing from 95° ethanol.

2-(4-(Aminomethyl)-1-piperidyl)-N-phenyl acetamide dihydrochloride (3.5 g) was thus obtained.

m.p.: 288° C. (dec.)

Elemental Analysis

For $C_{14}H_{21}N_3O.2HCl.H_2O$

|  | C | H | N |
|---|---|---|---|
| Found % | 49.73 | 7.55 | 12.21 |
| Calculated % | 49.71 | 7.45 | 12.42 |

$^1$H-NMR (δ, DMSO-$d_6$): 1.44-1.70 (m, 2H); 1.71-2.20 (m, 3H); 2.77 (s, 2H); 3.04-3.26 (m, 4H); 4.18 (s, 2H); 7.12 (t, J=7 Hz, 1H); 7.35 (t, J=7 Hz, 2H); 7.66 (d, J=7 Hz, 2H); 8.33 (broad s, 3H); 10.18 (s, 1H); 11.07 (s, 1H).

EXAMPLE 2

N3-((1-(2-oxo-2-(phenylamino)ethyl)-4-piperidyl)methyl)-1-(1-methylethyl)-1H-indazole-3-carboxamide hydrochloride (AF3R172)

Compound I: R1=R3=R4=R5=R6=R7=R8=H, R2=i-$C_3H_7$, X=C(O)NH 1-(1-Methylethyl)-1H-indazole-3-carboxyl chloride (17.5 g; 0.079 mol) prepared as described in EP-A-0 975 623 was added portionwise to a suspension of the product prepared as described in Example 1b) (19.5 g; 0.079 mol) in toluene (300 ml).

The reaction mixture was stirred at room temperature for 6 hours. The solvent was then removed by evaporation under reduced pressure. The residue was taken up in 1N NaOH (100 ml) and dichloromethane (100 ml) and transferred into a separating funnel.

The organic phase was separated out and dried over $Na_2SO_4$. The solvent was then removed by evaporation under reduced pressure and the residue thus obtained (20 g) was purified by flash chromatography, eluting with a 7/3 hexane/ethyl acetate mixture.

The product obtained was converted into the corresponding hydrochloride by dissolving in ethyl acetate, adding hydrochloric ethanol and crystallizing from a 9/1 mixture of ethyl acetate/absolute ethanol.

The desired product (12.8 g) was thus obtained.

m.p.: 201-202° C. (dec.)

Elemental Analysis

For $C_{25}H_{31}N_5O_2 \cdot HCl$

|  | C | H | N |
|---|---|---|---|
| Found % | 63.83 | 6.74 | 14.75 |
| Calculated % | 63.89 | 6.86 | 14.90 |

$^1$H-NMR (δ, DMSO-d$_6$): 1.55 (d, J=7 Hz, 6H); 1.50-2.10 (m, 5H); 3.00-3.70 (m, 6H); 4.16 (s, 2H); 5.08 (septet, J=7 Hz, 1H); 7.11 (t, J=7 Hz, 1H); 7.20-7.50 (m, 4H); 7.66 (d, J=8 Hz, 2H); 7.79 (d, J=8 Hz, 1H); 8.18 (d, J=8 Hz, 1H); 8.37 (t, J=6 Hz, 1H); 10.03 (broad s, 1H); 11.04 (s, 1H).

EXAMPLE 3

N3-((1-(2-oxo-2-(phenylamino)ethyl)-4-piperidyl)methyl)-1H-indazole-3-carboxamide tosylate (AF3R276)

Compound I: R1=R2=R3=R4=R5=R6=R7=R8=H, X=C(O)NH

A solution of the product prepared as described in Example 1b) (5.7 g; 0.026 mol) in dichloromethane (30 ml) was added, via a dropping funnel, to a suspension of 7H,14H-indazolo[2',3':4,5]pyrazino[1,2-b]indazole-7,14-dione (3.7 g; 0.013 mol), prepared as described in J. O. C. 1958, Vol. 23, p. 621, in toluene (30 ml).

After stirring at room temperature for 18 hours, the reaction mixture was transferred into a separating funnel. Dichloromethane (30 ml) was added and the organic phase was washed with 1N NaOH. The organic phase was separated out and dried over $Na_2SO_4$. The solvent was then removed by evaporation under reduced pressure and the product thus obtained was converted into the corresponding tosylate by dissolving in ethyl acetate, adding a stoichiometric amount of p-toluenesulphonic acid and recrystallizing from 95° ethanol.

The desired product (4.3 g) was thus obtained.

m.p.: 215.5-217.5° C.

Elemental Analysis

For $C_{22}H_{25}N_5O_2 \cdot C_7H_8O_3S \cdot 1/2H_2O$

|  | C | H | N |
|---|---|---|---|
| Found % | 60.71 | 5.92 | 12.24 |
| Calculated % | 60.82 | 5.98 | 12.23 |

$^1$H-NMR (δ, DMSO-d$_6$): 1.48-1.73 (m, 2H); 1.77-2.10 (m, 3H); 2.28 (s, 3H); 2.93-3.65 (m, 6H); 4.10 (s, 2H); 7.07-7.67 (m, 12H); 8.18 (d, J=8 Hz, 1H); 8.53 (t, J=6 Hz, 1H); 9.63 (broad s, 1H); 10.52 (s, 1H); 13.57 (s, 1H).

EXAMPLE 4

N3-((1-(2-oxo-2-(phenylamino)ethyl)-4-piperidyl)methyl)-1-benzyl-1H-indazole-3-carboxamide hydrochloride (AF3R277)

Compound I: R1=R3=R4=R5=R6=R7=R8=H, R2=C$_6$H$_5$CH$_2$, X=C(O)NH a) 1-benzyl-1H-indazole-3-carboxyl chloride Thionyl chloride (5.6 ml; 0.077 mol) was added to a suspension of 1-benzyl-1H-indazole-3-carboxylic acid (6.5 g; 0.026 mol), prepared as described in J. Med. Chem., 1976, Vol. 19 (6), pp. 778-783, in toluene (65 ml), and the reaction mixture was refluxed for 2 hours. The solvent was removed by evaporation under reduced pressure and the residue was taken up twice with toluene (2×50 ml) to give the desired product (7 g), which was used without further purification.

b) N3-((1-(2-oxo-2-(phenylamino)ethyl)-4-piperidyl)methyl)-1-benzyl-1H-indazole-3-carboxamide hydrochloride By working in a manner similar to that described in Example 2, the product prepared as described in Example 4a) (8.2 g; 0.030 mol) was reacted with the product as described in Example 1b) (7.5 g; 0.030 mol) and the reaction product was converted into the corresponding hydrochloride.

The desired product (4.5 g) was thus obtained.

m.p.: 196-198° C.

Elemental Analysis

For $C_{29}H_{31}N_5O_2 \cdot HCl \cdot 1/2H_2O$

|  | C | H | N |
|---|---|---|---|
| Found % | 66.19 | 6.28 | 13.24 |
| Calculated % | 66.09 | 6.31 | 13.29 |

$^1$H-NMR (δ, CDCl$_3$): 1.64-2.40 (m, 5H); 3.10-3.77 (m, 6H); 4.13 (s, 2H); 5.58 (s, 1H); 7.00-7.40 (m, 13H); 7.74 (d, J=8 Hz, 1H); 8.34 (d, J=8 Hz, 1H); 10.88 (s, 1H); 11.26 (broad s, 1H).

EXAMPLE 5

N3-((1-(2-oxo-2-((4-((phenylmethyl)oxy)phenyl)amino)ethyl)-4-piperidyl)methyl)-1-(1-methylethyl)-1H-indazole-3-carboxamide (AF3R331)

Compound I: R1=R4=R5=R6=R7=R8=H, R2=I-C$_3$H$_7$, R3=4-OCH$_2$C$_6$H$_5$, X=C(O)NH a) N1-(4-((phenylmethyl)oxy)phenyl)-2-(4-(aminomethyl)-1-piperidyl)ethanamide hydrochloride The product prepared as described in Example 1a) (68 g; 0.34 mol) was reacted with N1-(4-((phenylmethyl)oxy)phenyl)-2-chloroethanamide (93.7 g; 0.34 mol), prepared as described in Indian J. Appl. Chem. 1967, Vol. 30(3-4), pp. 91-95, working in a manner similar to that described in Example 1b).

The oily residue (120 g) thus obtained was purified by flash chromatography, eluting with a 10/4/1 chloroform/methanol/aqueous ammonia mixture.

N1-(4-((Phenylmethyl)oxy)phenyl)-2-(4-(aminomethyl)-1-piperidyl)ethanamide base (70 g) was thus obtained, which was converted into the corresponding dihydrochloride by dissolving in ethanol, adding hydrochloric ethanol and recrystallizing from absolute ethanol to give 65 g of the desired product.

Elemental Analysis:
For $C_{21}H_{27}N_3O_2 \cdot 2HCl$

|  | C | H | N |
|---|---|---|---|
| Found % | 58.88 | 6.75 | 9.55 |
| Calculated % | 59.16 | 6.86 | 9.85 |

$^1$H-NMR (δ, DMSO-d$_6$): 1.45-1.70 (m, 2H); 1.70-2.20 (m, 3H); 2.72 (s, 2H); 3.02-3.68 (m, 4H); 4.12 (s, 2H); 5.08 (s, 2H); 7.00 (d, J=9 Hz, 2H); 7.26-7.48 (m, 5H); 8.56 (d, J=9 Hz, 2H); 8.27 (s, 3H); 10.14 (s, 1H); 10.92 (s, 1H).

b) N3-((1-(2-oxo-2-((4-((phenylmethyl)oxy)phenyl)amino)ethyl)-4-piperidyl)methyl)-1-(1-methylethyl)-1H-indazole-3-carboxamide 1-(1-Methylethyl)-1H-indazole-3-carboxyl chloride (31.1 g; 0.14 mol), prepared as described in EP-A-0 975 623, was added portionwise to a suspension of N1-(4-((phenylmethyl)oxy)phenyl)-2-(4-(aminomethyl)-1-piperidyl)ethanamide, prepared as described in Example 5a) (49.5 g; 0.14 mol), in toluene (500 ml).

The reaction mixture was stirred at room temperature for 6 hours and then filtered. The solid thus obtained was taken up in 2N NaOH and dichloromethane. The mixture was transferred into a separating funnel. The organic phase was separated out and dried over Na$_2$SO$_4$. The solvent was removed by evaporation under reduced pressure and the residue thus obtained (75 g) was crystallized twice from isopropanol to give 56 g of the desired product.
m.p.: 113-115° C.
Elemental Analysis
For $C_{32}H_{37}N_5O_3$

|  | C | H | N |
|---|---|---|---|
| Found % | 71.03 | 7.19 | 12.95 |
| Calculated % | 71.22 | 6.91 | 12.98 |

$^1$H-NMR (δ, DMSO-d$_6$): 1.24-1.44 (m, 2H); 1.54 (d, J=7 Hz, 6H); 1.48-1.78 (m, 3H); 2.10 (t, J=11 Hz, 2H); 2.87 (d, J=11 Hz, 2H); 3.05 (s, 2H); 3.24 (t, J=6 Hz, 2H); 5.07 (septet, J=7 Hz, 1H); 5.07 (s, 2H); 6.96 (d, J=9 Hz, 2H); 7.20-7.48 (m, 7H); 7.54 (d, J=9 Hz, 2H); 7.78 (d, J=9 Hz, 1H); 8.19 (d, J=8 Hz, 1H); 8.23 (t, J=6 Hz, 1H); 9.52 (s, 1H).

EXAMPLE 6

N3-((1-(2-((4-hydroxyphenyl)amino)-2-oxoethyl)-4-piperidyl)methyl)-1-(1-methylethyl)-1H-indazole-3-arboxamide hydrochloride (AF3R278)

Compound I: R1=R4=R5=R6=R7=R8=H,
R2=i-C$_3$H$_7$, R3=4-OH, X=C(O)NH

A solution of the product prepared as described in Example 5 (36.5 g; 0.068 mol) in 950 ethanol (1000 ml) was hydrogenated over 10% Pd—C (3.65 g) at 40 psi for 5 hours. The reaction mixture was then filtered and the filtrate was concentrated under reduced pressure.

The product thus obtained was converted into the corresponding hydrochloride by dissolving in absolute ethanol, adding hydrochloric ethanol and recrystallizing from absolute ethanol, to give 20 g of the desired product.
m.p.: 277° C. (dec.)
Elemental Analysis
For $C_{25}H_{31}N_5O_3 \cdot HCl$

|  | C | H | N |
|---|---|---|---|
| Found % | 61.76 | 6.76 | 14.44 |
| Calculated % | 61.78 | 6.64 | 14.41 |

$^1$H-NMR (δ, DMSO-d$_6$): 1.55 (d, J=7 Hz, 6H); 1.46-1.75 (m, 2H); 1.75-2.10 (m, 3H); 2.95-3.64 (m, 6H); 4.07 (s, 2H); 5.08 (septet, J=7 Hz, 1H); 6.75 (d, J=9 Hz, 2H); 7.20-7.31 (m, 1H); 7.35-7.49 (m, 3H); 7.79 (d, J=9 Hz, 1H); 8.17 (dt, J=8; 1 Hz, 1H); 8.36 (t, J=6 Hz, 1H); 9.37 (s, 1H); 9.89 (broad s, 1H); 10.62 (s, 1H).

EXAMPLE 7

N3-((1-(2-oxo-2-((4-nitrophenyl)amino)ethyl)-4-piperidyl)methyl)-1-(1-methylethyl)-1H-indazole-3-carboxamide (AF3R335)

Compound I: R1=R4=R5=R6=R7=R8=H,
R2=i-C$_3$H$_7$, R3=4-NO$_2$, X=C(O)NH a) 2-(4-(aminomethyl)-1-piperidyl)-N-(4-nitrophenyl)acetamide The product prepared as described in Example 1a) (28 g; 0.14 mol) was reacted with N1-(4-nitrophenyl)-2-chloroethanamide (30 g; 0.14 mol), working in a manner similar to that described in Example 1b).

An oily residue (20 g) was thus obtained, and was purified by flash chromatography, eluting with a 10/4/1 chloroform/methanol/aqueous ammonia mixture to give 15 g of the desired product.
Elemental Analysis
For $C_{14}H_{20}N_4O_3$

|  | C | H | N |
|---|---|---|---|
| Found % | 57.23 | 7.00 | 18.98 |
| Calculated % | 57.52 | 6.90 | 19.16 |

$^1$H-NMR (δ, DMSO-d$_6$+D$_2$O): 1.20-1.40 (m, 2H); 1.48-1.78 (m, 3H); 2.17 (t, J=12 Hz, 2H); 2.72 (d, J=7 Hz, 2H); 2.89 (d, J=12 Hz, 2H); 3.21 (s, 2H); 7.90 (d, J=9 Hz, 2H); 8.23 (d, J=9 Hz, 2H).

b) N3-((1-(2-oxo-2-((4-nitrophenyl)amino)ethyl)-4-piperidyl)methyl)-1-(1-methylethyl)-1H-indazole-3-carboxamide 1-(1-Methylethyl)-1H-indazole-3-carboxyl chloride (3.1 g; 0.013 mol), prepared as described in EP-A-0 975 623, was added portionwise to a suspension of the product prepared according to Example 7a) (4.07 g, 0.014 mol) in toluene (300 ml).

The reaction mixture was stirred at room temperature for 6 hours. The solvent was then removed by evaporation under reduced pressure. The residue was taken up in 1N NaOH and dichloromethane. The mixture was transferred into a separating funnel. The organic phase was separated out and dried over $Na_2SO_4$. The solvent was removed by evaporation under reduced pressure. The residue thus obtained was purified by flash chromatography, eluting with ethyl acetate, to give 2.8 g of the desired product.

Elemental Analysis

For $C_{25}H_{30}N_6O_4$

|  | C | H | N |
|---|---|---|---|
| Found % | 62.62 | 6.38 | 17.33 |
| Calculated % | 62.75 | 6.32 | 17.56 |

$^1$H-NMR ($\delta$, $CDCl_3$): 1.36-1.55 (m, 2H); 1.61 (d, J=7 Hz, 6H); 1.66-1.98 (m, 3H); 2.32 (td, J=12; 2 Hz, 2H); 2.95 (d, J=12 Hz, 2H); 3.13 (s, 2H); 3.46 (t, J=7 Hz, 2H); 4.89 (septet, J=7 Hz, 1H); 7.19 (t, J=6 Hz, 1H); 7.23-7.30 (m, 1H); 7.35-7.50 (m, 2H); 7.75 (d, J=9 Hz, 2H); 8.21 (d, J=9 Hz, 2H); 8.38 (dt, J=8; 1 Hz, 1H); 9.60 (s, 1H).

EXAMPLE 8

5-methyl-N-3-((1-(2-oxo-2-(phenylamino)ethyl)-4-piperidyl)methyl)-1H-indazole-3-carboxamide hydrochloride (AF3R295)

Compound I: R1=$CH_3$,
R2=R3=R4=R5=R6=R7=R8=H, X=C(O)NH a) 2,9-dimethyl-7H,14H-indazolo[2',3':4,5]pyrazino[1,2-b]indazole-7,14-dione Thionyl chloride (11 ml; 0.151 mol) was added to a suspension of 5-methyl-1H-indazole-3-carboxylic acid (12.2 g; 0.056 mol), prepared as described in J. Heterocyclic Chem. 1964, Vol. 1 (5) 239-241, in toluene (130 ml), and the reaction mixture was refluxed for 4 hours. The solvent was removed by evaporation under reduced pressure and the residue was taken up twice in toluene to give 12 g of the desired product.

$^1$H-NMR ($\delta$, $CDCl_3$): 2.54 (d, J=1 Hz, 6H); 7.35 (dd, J=9; 2 Hz, 2H); 7.85 (d, J=9 Hz, 2H); 8.01 (m, 1H).

b) 5-methyl-N-3-((1-(2-oxo-2-(phenylamino)ethyl)-4-piperidyl)methyl)-1H-indazole-3-carboxamide hydrochloride The product prepared according to Example 1b) (4.5 g; 0.018 mol) and the product prepared according to Example 8a) (2.8 g; 0.009 mol) were reacted in a manner similar to that described in Example 3.

3.8 g of 5-methyl-N-3-((1-(2-oxo-2-(phenylamino)ethyl)-4-piperidyl)methyl)-1H-indazole-3-carboxamide were thus obtained, and were converted into the corresponding hydrochloride by dissolving in ethyl acetate, adding hydrochloric ethanol and recrystallizing from a 95/5 ethyl acetate/ethanol mixture to give 2.7 g of the desired product.

m.p.: 252° C. (dec.)

Elemental Analysis

For $C_{23}H_{27}N_5O_2 \cdot HCl$

|  | C | H | N |
|---|---|---|---|
| Found % | 62.62 | 6.38 | 15.70 |
| Calculated % | 62.51 | 6.39 | 15.85 |

$^1$H-NMR ($\delta$, DMSO-$d_6$): 1.50-1.72 (m, 2H); 1.80-2.00 (m, 3H); 2.43 (s, 3H); 2.96-3.64 (m, 6H); 4.13 (s, 2H); 7.12 (t, J=7 Hz, 1H); 7.24 (dd J=9; 1.5 Hz, 1H); 7.36 (t, J=7 Hz, 2H); 7.50 (d, J=9 Hz, 1H); 7.62 (d, J=7 Hz, 2H); 7.95 (s, 1H); 8.46 (t, J=6 Hz, 1H); 9.86 (broad s, 1H); 10.52 (s, 1H); 13.51 (s, 1H).

EXAMPLE 9

5-methyl-N-3-((1-(2-oxo-2-(phenylamino)ethyl)-4-piperidyl)methyl)-1-(1-methylethyl)-1H-indazole-3-carboxamide hydrochloride (AF3R299)

Compound I: R1=$CH_3$, R2=i-$C_3H_7$,
R3=R4=R5=R6=R7=R8=H, X=C(O)NH a) isopropyl 1-(1-methylethyl)-5-methyl-1H-indazole-3-carboxylate A 60% suspension of sodium hydride in mineral oil (17.1 g; 0.43 mol) was added to a suspension of 5-methyl-1H-indazole-3-carboxylic acid (30 g; 0.17 mol), prepared as described in J. Heterocyclic Chem. 1964, Vol. 1 (5) 239-241, in dimethylformamide (450 ml), and the reaction mixture was heated to 70° C. After 30 minutes, isopropyl bromide (48 ml, 0.51 mol) was added.

The reaction mixture was stirred for 6 hours at 70° C. After cooling, water was added. The reaction mixture was transferred into a separating funnel and extracted with diethyl ether. The organic phase was washed with saturated sodium bicarbonate solution and the solvent was finally removed by evaporation under reduced pressure.

20 g of an oil were thus obtained, and were purified by flash chromatography, eluting with a 7/3 hexane/ethyl acetate mixture, to give 12 g of the desired product.

$^1$H-NMR ($\delta$, $CDCl_3$): 1.47 (d, J=6 Hz, 6H); 1.64 (d, J=7 Hz, 6H); 2.50 (d, J=1 Hz, 3H); 4.92 (septet, J=7 Hz, 1H); 5.39 (septet, J=6 Hz, 1H); 7.23 (dd, J=9; 1 Hz, 1H); 7.40 (d, J=9 Hz, 1H); 7.95 (quintet, J=1 Hz, 1H).

b) 1-(1-methylethyl)-5-methyl-1H-indazole-3-carboxylic acid

A suspension of the product prepared according to Example 9a) (8 g, 0.03 mol) in 1 M NaOH (42 ml) was refluxed for 3 hours. It was then poured into water, acidified with 2M HCl and extracted with dichloromethane. After evaporating off the solvent under reduced pressure, 7 g of the desired product were obtained.

$^1$H-NMR ($\delta$, $CDCl_3$): 1.61 (d, J=7 Hz, 6H); 2.44 (s, 3H); 4.88 (septet, J=7 Hz, 1H); 7.19 (d, J=9 Hz, 1H); 7.34 (d, J=9 Hz, 1H); 7.97 (s, 1H); 9.32 (broad s, 1H).

c) 1-(1-methylethyl)-5-methyl-1H-indazole-3-carboxyl chloride

The product prepared according to Example 9a) (12.2 g; 0.056 mol) was chlorinated in a manner similar to that described in Example 4a).

13.3 g of the desired product were thus obtained, and were used without further purification.

d) 5-methyl-N-3-((1-(2-oxo-2-(phenylamino)ethyl)-4-piperidyl)methyl)-1-(1-methylethyl)-1H-indazole-3-carboxamide hydrochloride The product prepared according to Example 1b) (3 g; 0.012 mol) was added to a suspension of the product prepared according to Example 9c) (2.9 g; 0.012 mol) in toluene (60 ml).

The reaction mixture was stirred at room temperature for 6 hours and the solvent was then removed under reduced pressure. The residue was taken up in 2N NaOH and dichloromethane. The mixture was transferred into a separating funnel. The organic phase was separated out and dried over $Na_2SO_4$. The solvent was removed by evaporation under reduced pressure. The residue thus obtained (4 g) was purified by flash chromatography, eluting with a 97/3 chloroform/methanol mixture. The product obtained was converted into the corresponding hydrochloride by dissolving in ethyl acetate, adding hydrochloric ethanol and crystallizing from absolute ethanol, to give 2.3 g of the desired product.

m.p.: 241° C. (dec.)
Elemental Analysis
For $C_{26}H_{33}N_5O_2.HCl$

|  | C | H | N |
|---|---|---|---|
| Found % | 64.69 | 7.09 | 14.44 |
| Calculated % | 64.52 | 7.08 | 14.47 |

$^1$H-NMR (δ, DMSO-d$_6$): 1.59 (d, J=7 Hz, 6H); 1.78-2.25 (m, 5H); 2.47 (s, 3H); 3.06-3.27 (m, 2H); 3.41 (t, J=6 Hz, 2H); 3.56-3.77 (m, 2H); 4.01 (s, 2H); 4.83 (septet, J=7 Hz, 1H); 7.06-7.39 (m, 6H); 7.76 (d, J=8 Hz, 2H); 8.12 (s, 1H); 10.91 (s, 1H); 11.79 (broad s, 1H).

EXAMPLE 10

N3-((1-(2-oxo-2-((4-(dimethylamino)phenyl)amino)ethyl)-4-piperidyl)methyl)-1-(1-methylethyl)-1H-indazole-3-carboxamide dihydrochloride (AF3R301)

Compound I: R1=R4=R5=R6=R7=R8=H,
R2=i-$C_3H_7$, R3=4N(CH$_3$)$_2$, X=C(O)NH a) 2-(4-(aminomethyl)-1-piperidyl)-N-(4-(dimethylamino)phenyl)-acetamide

The product prepared according to Example 1a) (25 g; 0.12 mol) was reacted with N1-(4-(dimethylamino)phenyl)-2-chloroethanamide (25.5 g; 0.12 mol) in a manner similar to that described in Example 1b).

36 g of an oily residue were obtained, and were purified by flash chromatography, eluting with a 10/4/1 chloroform/methanol/aqueous ammonia mixture to give 25 g of the desired product.

Elemental Analysis:
For $C_{16}H_{25}N_4O$

|  | C | H | N |
|---|---|---|---|
| Found % | 66.53 | 9.30 | 18.97 |
| Calculated % | 66.17 | 9.02 | 19.29 |

$^1$H-NMR (δ, DMSO-d$_6$+D$_2$O): 1.18-1.50 (m, 2H); 1.55-1.78 (m, 3H); 2.15-2.35 (m, 2H); 2.80-3.10 (m, 10H); 3.34 (s, 2H); 6.67 (d, J=9 Hz, 2H); 7.39 (d, J=9 Hz, 2H).

b) N3-((1-(2-oxo-2-((4-dimethylamino)phenyl)amino)ethyl)-4-piperidyl)methyl)-1-(1-methylethyl)-1H-indazole-3-carboxamide dihydrochloride By working in a manner similar to that described in Example 2, the product prepared according to Example 10a) (6.4 g; 0.022 mol) was reacted with 1-(1-methylethyl)-1H-indazole-3-carboxyl chloride (4.9 g; 0.022 mol) and the reaction product was converted into the corresponding hydrochloride.

4.2 g of the desired product were thus obtained.
m.p.: 203° C. (dec.)
Elemental Analysis
For $C_{26}H_{36}N_6O_2.2HCl.H_2O$

|  | C | H | N |
|---|---|---|---|
| Found % | 57.18 | 7.17 | 14.68 |
| Calculated % | 57.14 | 7.10 | 14.81 |

$^1$H-NMR (δ, CDCl$_3$): 1.61 (d, J=7 Hz, 6H); 1.78-2.30 (m, 5H); 3.16 (s, 6H); 3.00-3.90 (m, 6H); 4.31 (s, 2H); 4.90 (septet, J=7 Hz, 1H); 7.25 (t, J=8 Hz, 1H); 7.35-7.46 (m, 2H); 7.49 (d, J=9 Hz, 1H); 7.70 (d, J=9 Hz, 2H); 7.86 (d, J=9 Hz, 2H); 8.30 (d, J=8 Hz, 1H); 10.65 (broad s, 2H); 11.55 (s, 1H).

EXAMPLE 11

N3-((1-(2-oxo-2-((2,6-dimethylphenyl)amino)ethyl)-4-piperidyl)methyl)-1-(1-methylethyl)-1H-indazole-3-carboxamide oxalate (AF3R305)

Compound I: R1=R5=R6=R7=R8=H, R2=i-$C_3H_7$,
R3=2-$CH_3$, R4=6-$CH_3$, X=C(O)NH a) 2-(4-(aminomethyl)-1-piperidyl)-N-(2,6-dimethylphenyl)acetamide dihydrochloride The product prepared according to Example 1a) (32 g; 0.16 mol) was reacted with N1-(2,6-dimethylphenyl)-2-chloroethanamide (31.6 g; 0.16 mol) in a manner similar to that described in Example 1b).

54 g of a residue were thus obtained, and were crystallized from ethyl acetate to give 45 g of the desired product, which was converted into the corresponding hydrochloride by dissolving in ethyl acetate, adding hydrochloric ethanol and recrystallizing from 95° ethanol to give 40 g of the desired product.

Elemental Analysis
For $C_{16}H_{25}N_3O.2HCl$

|  | C | H | N |
|---|---|---|---|
| Found % | 55.12 | 7.77 | 20.22 |
| Calculated % | 55.17 | 7.81 | 20.36 |

$^1$H-NMR (δ, DMSO-$d_6$): 1.43-1.71 (m, 2H); 1.73-2.06 (m, 3H); 2.18 (s, 6H); 2.71 (s, 2H); 3.05-3.66 (m, 4H); 4.25 (s, 2H); 7.10 (s, 3H); 8.35 (broad s, 3H); 10.19 (broad s, 1H); 10.33 (s, 1H).

b) N3-((1-(2-oxo-2-((2,6-dimethylphenyl)amino) ethyl)-4-piperidyl)methyl)-1-(1-methylethyl)-1H-indazole-3-carboxamide oxalate 1-(1-Methylethyl)-1H-indazole-3-carboxyl chloride (11.3 g; 0.051 mol), prepared as described in EP-A-0 975 623, was added portionwise to a suspension of the product prepared as described in Example 11a), as base (14.1 g; 0.051 mol), in toluene (200 ml).

The reaction mixture was stirred at room temperature for 6 hours. After removing the solvent by evaporation under reduced pressure, the residue was taken up in 1N NaOH and dichloromethane. The mixture was transferred into a separating funnel. The organic phase was separated out and dried over $Na_2SO_4$. The solvent was removed by evaporation under reduced pressure. The residue thus obtained (20 g) was purified by flash chromatography, eluting with ethyl acetate. The product obtained was converted into the corresponding oxalate by dissolving in ethyl acetate, adding a stoichiometric amount of oxalic acid and crystallizing from 95° ethanol, to give 7.8 g of the desired product.
m.p.: 214° C. (dec.)
Elemental Analysis
For $C_{27}H_{35}N_5O_2.C_2H_2O_4$

|  | C | H | N |
|---|---|---|---|
| Found % | 63.09 | 6.80 | 12.73 |
| Calculated % | 63.14 | 6.76 | 12.70 |

$^1$H-NMR (δ, DMSO-$d_6$): 1.54 (d, J=7 Hz, 6H); 1.42-1.64 (m, 2H); 1.72-1.92 (m, 3H); 2.15 (s, 6H); 2.78 (t, J=12 Hz, 2H); 3.17-3.40 (m, 4H); 3.81 (s, 2H); 5.08 (septet, J=7 Hz, 1H); 6.20 (broad s, 2H); 7.09 (s, 3H); 7.20-7.30 (m, 1H); 7.38-7.48 (m, 1H); 7.79 (d, J=9 Hz, 1H); 8.17 (d, J=8 Hz, 1H); 8.31 (t, J=6 Hz, 1H); 9.68 (s, 1H).

EXAMPLE 12

N3-((1-(2-oxo-2-((4-aminophenyl)amino)ethyl)-4-piperidyl)methyl)-1-(1-methylethyl)-1H-indazole-3-carboxamide dihydrochloride (AF3R292)

Compound I: R1=R4=R5=R6=R7=R8=H, R2=i-$C_3H_7$, R3=4-$NH_2$, X=C(O)NH

A solution of the product prepared according to Example 7b) (1.4 g; 0.003 mol) in absolute ethanol (50 ml) was hydrogenated over 10% Pd—C (90 mg) at 40 psi for 3 hours. The mixture was then filtered and the filtrate was concentrated under reduced pressure. The product thus obtained was converted into the corresponding dihydrochloride by dissolving in ethyl acetate, adding hydrochloric ethanol and crystallizing from a 95/5 ethyl acetate/ethanol mixture, to give 0.7 g of the desired product.
m.p.: 252° C. (dec.)
Elemental Analysis
For $C_{25}H_{32}N_6O_2.2HCl.H_2O$

|  | C | H | N |
|---|---|---|---|
| Found % | 55.70 | 6.52 | 15.44 |
| Calculated % | 55.66 | 6.73 | 15.58 |

$^1$H-NMR (δ, DMSO-$d_6$): 1.55 (d, J=7 Hz, 6H); 1.40-2.09 (m, 5H); 2.96-3.71 (m, 6H); 4.16 (s, 2H); 5.00 (septet, J=7 Hz, 1H); 7.20-7.38 (m, 3H); 7.30-7.48 (m, 1H); 7.70 (d, J=9 Hz, 2H); 7.79 (d, J=9 Hz, 2H); 8.17 (d, J=8 Hz, 1H); 8.37 (t, J=6 Hz, 1H); 10.03 (broad s, 4H); 11.17 (s, 1H).

TESTS

1. CFA-induced Mechanical Hyperalgesia in Rats

Male CD rats weighing 150-200 g on arrival were used.

By means of an analgesimeter, rats with a response threshold to a mechanical nociceptive stimulus in the range from 150 to 180 g were selected. By applying a gradual increase in pressure onto the dorsal region of the left hind paw of the rat, the instrument makes it possible to record the nocifensive response, expressed in grams, corresponding to the moment at which the animal retracts the paw [Randall L O and Selitto J J. A method for the measurement of analgesic activity on inflamed tissue. Arch. Int. Pharmacodyn. Ther. 1957; 111: 409-419].

The hyperalgesia was induced by unilateral injection of 150 μl of "Complete Freund's Adjuvant" (CFA) into the surface of the left hind paw of the animal [Andrew D, Greenspan J D. Mechanical and heat sensitization of cutaneous nociceptors after peripheral inflammation in the rat. J Neurophysiol. 1999; 82(5): 2649-2656; Hargreaves K, Dubner R, Brown R, Flores C, Joris J. A new and sensitive method for measuring thermal nociception in cutaneous hyperalgesia. Pain 1988; 32: 77-88].

The test compounds were tested (dose: $10^{-5}$ mol/kg) by performing the test 23 hours after injecting the CFA.

One hour after the treatment, the pain threshold measured in control animals was compared with that measured in animals treated with the test product. The control animals were treated with the same vehicle (water) used for administering the test products. The results are illustrated in Table 1.

TABLE 1

Effect on CFA

| Treatment | No. of rats | Pain threshold (g) 1 h after the treatment |
|---|---|---|
| Vehicle | 12 | 120 ± 6.1 |
| AF3R172 | 12 | 175 ± 10.2 |
| AF3R278 | 12 | 164 ± 10.2 |
| AF3R301 | 12 | 151 ± 10.7 |
| AF3R276 | 12 | 185 ± 15.9 |
| AF3R277 | 12 | 170 ± 10.7 |
| AF3R295 | 12 | 202 ± 17.0 |
| AF3R299 | 12 | 167 ± 8.5 |
| AF3R305 | 12 | 174 ± 8.4 |
| AF3R292 | 12 | 154 ± 11.5 |
| AF3R331 | 12 | 156 ± 8.7 |
| AF3R335 | 12 | 168 ± 6.8 |

Pain threshold of normal animals of equivalent weight/age=155±2.1 g

2. Mechanical Hyperalgesia in Rats with Streptozotocin-induced Diabetes

Male CD rats weighing 240-300 g on arrival were used.

The diabetic syndrome was induced by means of a single intraperitoneal (i.p.) injection of 80 mg/kg of streptozotocin dissolved in sterile physiological solution [Courteix C, Eschalier A, Lavarenne J. Streptozotocin-induced diabetic rats: behavioural evidence for a model of chronic pain. Pain, 1993; 53: 81-88; Bannon A W, Decker M W, Kim D J, Campbell J E, Arneric S P. ABT-594, a novel cholinergic channel modulator, is efficacious in nerve ligation and diabetic neuropathy models of neuropathic pain. Brain Res. 1998; 801: 158-63].

At least three weeks after the injection of streptozotocin, rats with a level of glycemia≧300 mg/dl and with a response threshold to a mechanical nociceptive stimulus ≦120 g were selected. The glycemia levels were measured by means of a reflectometer, using reactive strips impregnated with glucose oxidase. The pain threshold was measured using an analgesimeter. By applying a gradual increase in pressure onto the dorsal area of the left hind paw of the rat, the instrument makes it possible to record the nocifensive response, expressed in grams, corresponding to the moment at which the animal retracts the paw.

Two hours after the treatment, the pain threshold measured in control animals was compared with that measured in animals treated with the test product (dose: $10^{-5}$ mol/kg).

The control animals were treated with the same vehicle (water) used for administering the test products. The results are illustrated in Table 2.

TABLE 2

Effect on diabetic neuropathy

| Treatment | No. of rats | Pain threshold (g) 2 h after the treatment |
| --- | --- | --- |
| Vehicle | 8 | 114 ± 2.7 |
| AF3R172 | 8 | 186 ± 13.0 |
| AF3R278 | 8 | 240 ± 16.5 |
| AF3R301 | 8 | 201 ± 13.8 |
| AF3R276 | 8 | 210 ± 10.9 |
| AF3R277 | 8 | 188 ± 11.0 |
| AF3R295 | 8 | 212 ± 14.6 |
| AF3R299 | 8 | 200 ± 10.7 |
| AF3R305 | 8 | 189 ± 9.2 |
| AF3R292 | 8 | 202 ± 8.7 |
| AF3R331 | 8 | 192 ± 11.5 |
| AF3R335 | 8 | 180 ± 13.0 |

Pain threshold of normal animals of equivalent weight/age=240±8.7 g

What we claim is:

1. A compound of formula (II):

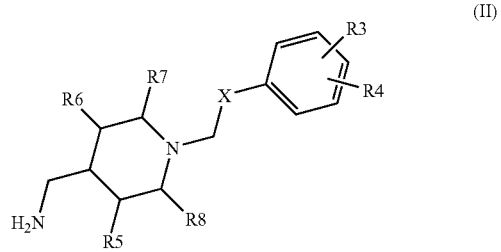

wherein
X is an NHC(O) or C(O)NH group,
R3 and R4, which may be identical or different, are a hydrogen or halogen atom, or an amino, nitro, hydroxyl, linear or branched $C_{1-3}$alkyl, $C_{1-3}$alkoxy, di($C_{1-3}$)alkylamino, acetylamino or phenyl-($C_{1-3}$)alkoxy group, or R3 and R4, together, form a 5- to 7-membered ring in which one or two of the said members may be a hetero atom selected from the group consisting of N, S and O, and
R5, R6, R7 and R8, which may be identical or different, are H or methyl.

2. A compound according to claim 1, wherein R3 is H, methyl, hydroxyl, benzyloxy, nitro, amino or dimethylamino.

3. A compound according to claim 1, wherein R4 is H or methyl.

4. A compound according to claim 1, wherein R5, R6, R7 and R8 are H.

5. A compound according to claim 1, wherein R3 is H, methyl, hydroxyl, amino or dimethylamino.

6. A compound according to claim 1, wherein R4 is H, methyl or hydroxyl.

7. A compound according to claim 1, wherein:
R3 is H, methyl, hydroxyl, benzyloxy, nitro, amino, or dimethylamino;
R4 is H, methyl or hydroxyl; and
R5, R6, R7, and R8 are H.

8. A compound according to claim 1, wherein:
R3 is H, methyl, hydroxyl, amino, or dimethylamino;
R4 is H or methyl; and
R5, R6, R7, and R8 are H.

9. A compound of formula (II):

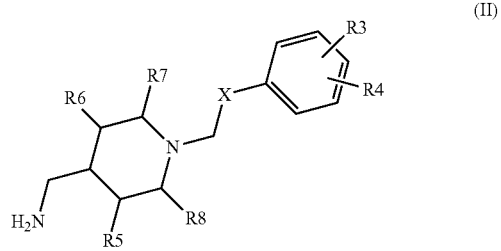

wherein
X is an NHC(O) or C(O)NH group,
R3 and R4, which may be identical or different, are a hydrogen or halogen atom, or an amino, nitro, hydroxyl, linear or branched $C_{1-3}$alkyl, $C_{1-3}$alkoxy, di($C_{1-3}$)alkylamino, acetylamino or phenyl-($C_{1-3}$)alkoxy group, and
R5, R6, R7 and R8, which may be identical or different, are H or methyl.

10. A compound according to claim 9, wherein R3 is H, methyl, hydroxyl, benzyloxy, nitro, amino or dimethylamino.

11. A compound according to claim 9, wherein R4 is H or methyl.

12. A compound according to claim 9, wherein R5, R6, R7 and R8 are H.

13. A compound according to claim 9, wherein R3 is H, methyl, hydroxyl, amino or dimethylamino.

14. A compound according to claim 9, wherein R4 is H, methyl or hydroxyl.

15. A compound according to claim 9, wherein:
R3 is H, methyl, hydroxyl, benzyloxy, nitro, amino, or dimethylamino;
R4 is H, methyl or hydroxyl; and
R5, R6, R7, and R8 are H.

16. A compound according to claim 9, wherein:
R3 is H, methyl, hydroxyl, amino, or dimethylamino;
R4 is H or methyl; and
R5, R6, R7, and R8 are H.

\* \* \* \* \*

UNITED STATES PATENT AND TRADEMARK OFFICE
CERTIFICATE OF CORRECTION

PATENT NO. : 8,519,139 B2  
APPLICATION NO. : 12/607463  
DATED : August 27, 2013  
INVENTOR(S) : Maria Alessandra Alisi et al.

Page 1 of 1

It is certified that error appears in the above-identified patent and that said Letters Patent is hereby corrected as shown below:

On the title page, Item (73), the Assignee information is incorrect. Item (73) should read:

--(73) Assignee: Aziende Chimiche Riunite Angelini Francesco A.C.R.A.F. S.p.A., Rome (IT)--

Signed and Sealed this  
Fifteenth Day of October, 2013

Teresa Stanek Rea  
*Deputy Director of the United States Patent and Trademark Office*